United States Patent [19]

Ramey et al.

[11] 4,007,156

[45] Feb. 8, 1977

[54] ACYLATED DERIVATIVES OF SUBSTITUTED PIPERAZINES AND POLYMERIC COMPOSITIONS STABILIZED THEREBY

[75] Inventors: Chester E. Ramey, Spring Valley; John J. Luzzi, Carmel, both of N.Y.

[73] Assignee: Ciba-Geigy Corporation, Ardsley, N.Y.

[22] Filed: June 27, 1975

[21] Appl. No.: 591,221

Related U.S. Application Data

[63] Continuation of Ser. No. 379,289, July 16, 1973, abandoned, which is a continuation-in-part of Ser. No. 249,025, May 1, 1972, abandoned.

[52] U.S. Cl. .................... 260/45.8 N; 260/268 TR; 260/268 C
[51] Int. Cl.² ........................................ C07D 241/36
[58] Field of Search ................ 260/268 TR, 45.8 N

[56] References Cited

UNITED STATES PATENTS

| 3,318,876 | 5/1967 | Cignarella et al. | 260/268 C |
| 3,899,491 | 8/1975 | Ramey et al. | 260/268 DK |
| 3,920,659 | 11/1975 | Ramey et al. | 260/268 DK |
| 3,928,330 | 12/1975 | Ramey et al. | 260/268 DK |
| 3,928,357 | 12/1975 | Ramey et al. | 260/268 DK |

*Primary Examiner*—Donald G. Daus
*Assistant Examiner*—Jose Tovar
*Attorney, Agent, or Firm*—Charles W. Vanecek

[57] ABSTRACT

Acylated derivatives of substituted piperazines are stabilizers for synthetic polymeric materials normally subject to deterioration caused by ultraviolet light. The compounds are prepared by the acylation reaction between a substituted piperazine and a mono or di-acid halide, ester or isocyanate. Polymeric compositions containing these stabilizers may also contain a hindered phenolic compound. A typical embodiment is 15-stearoyl-7,15-diazadispiro[5,1,5,3]hexadecane.

23 Claims, No Drawings

ACYLATED DERIVATIVES OF SUBSTITUTED PIPERAZINES AND POLYMERIC COMPOSITIONS STABILIZED THEREBY

RELATED APPLICATIONS

This application is a continuation of application Ser. No. 379,289, filed July 16, 1973, now abandoned, which is a continuation-in-part of Application Ser. No. 249,025, filed May 1, 1972, now abandoned.

BACKGROUND OF THE INVENTION

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirably physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It has been proposed to stabilize polymeric materials against ultraviolet light deterioration by the use of various types of ultraviolet absorbers. Thus, U.S. Pat. No. 3,004,896 discloses for this purpose 2(2-hydroxyphenyl)benzotriazole derivatives, while U.S. Pat. No. 3,189,630 discloses certain metal salts of hydroxybenzoic acids which are useful as actinic stabilizers in synthetic polymers.

DETAILED DISCLOSURE

The present invention is directed to a class of ultraviolet light stabilizers which consist of a compound of the formula

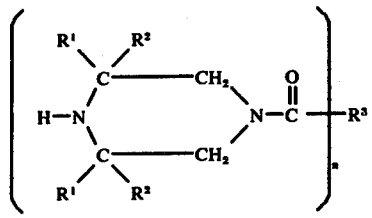

wherein $R^1$ and $R^2$ are independently of each other methyl or ethyl or together with the carbon to which they are bound form a cyclopentyl or cyclohexyl ring, which is unsubstituted or substituted with a methyl group;

$n$ is an integer of from 1 to 2;

when $n$ is 1, $R^3$ is an alkyl group containing from 1 to 24 carbon atoms, a phenyl group, or a group having the formula

wherein $R^4$ is an alkyl group containing from 1 to 24 carbon atoms or phenyl;

when $n$ is 2, $R^3$ is an alkylene group containing from 1 to 10 carbon atoms, a carbon to carbon bond, a phenylene group or the group having the formula

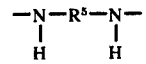

wherein $R^5$ is an alkylene group containing from 1 to 10 carbon atoms, a phenylene or (lower)alkyl substituted phenylene group.

By the term alkyl as represented by $R^1$ and $R^2$ is intended methyl or ethyl, with methyl being the preferred substituent. Representative of the cycloalkyl groups, as represented by $R^1$ and $R^2$, are cyclohexyl, cyclopentyl, 2-methyl, 3-methyl and 4-methylcyclohexyl, and 2-methyl and 3-methylcyclopentyl. The preferred cycloalkyl groups are cyclohexyl and 2-methylcyclohexyl.

This invention also relates to compositions of matter which are stabilized against ultraviolet light deterioration which comprises a synthetic organic polymer normally subject to ultraviolet deterioration containing from about 0.005% to 5% by weight of the polymer of the compounds of formula I and preferably from 0.01% to 2% by weight.

The compounds as represented by formula I can be used in combination with other light stabilizers such as 2-(2-hydroxyphenyl)benzotriazoles, 2-hydroxybenzophenones, nickel complexes and benzoates.

The stabilizers of this invention are suitable for the protection of many synthetic polymers from the deleterious effects of light. Homopolymers, copolymers, and mixtures thereof are embraced within the scope of substrates which may be stabilized with the stabilizers of this invention, along which may be mentioned, polystyrene and including homopolystyrene and copolymers with acrylonitrile and/or butadiene; vinyl resins formed from the polymerization of vinyl halides or from copolymerization of vinyl halides and unsaturated polymerizable compounds, for example, vinyl esters, α,β-unsaturated acids, α,β-unsaturated esters, and unsaturated hydrocarbons such as butadienes and styrene; poly-α-olefins such as high and low density polyethylene, cross-linked polyethylene, polypropylene, poly(4-methyl-pentene-1), polybutene-1, and the like including copolymers of poly-α-olefins such as ethylene-propylene copolymers and the like; polybutadiene, polyisoprene, polyurethanes such as are prepared from polyols and organic polyisocyanate; polyamides such as hexamethylene-adipamide; polyesters such as polymethyleneterephthalates; polycarbonates such as those prepared from bisphenol-A and phosgene; polyacetals; polyethylene oxide; and polyacrylics such as polyacrylonitrile; polyphenyleneoxides such as those prepared from 2,6-di-methylphenol and the like. Particularly preferred polymers for the compositions of this invention are those normally solid polymers of alpha-olefins having up to 3 carbon atoms, e.g., ethylene, propylene and their copolymers.

The stabilized polymers of the present invention have utility in the normal uses for which plastics are employed and are particularly useful for film and fiber. Compounds of this invention may be incorporated in the polymeric substance during the usual processing operations, for example, by hot milling, the composition then being extruded, pressed, blow molded or the like into films, fibers, filaments, hollow spheres and the like. Where the polymer is prepared from a liquid monomer as in the case of styrene, the stabilizer may be dispersed or dissolved in the monomer prior to polymerization or curing.

In addition to the actinic stabilizers described, the plastic compositions may contain other additives such as plasticizers, pigments, fillers, dyes, glass or other fibers, thermal antioxidants, and the like. For example in most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results are obtained with the preferred class of thermal antioxidants, the hindered phenols. These compounds have been found to provide the best thermal stabilization with the least discoloration in the compositions of the invention. Typical of these phenolic antioxidants include the following:

1. Phenolic compounds having the general formula
   Q-(CH₂)_w-A wherein
Q is

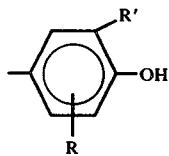

A is - CR(COOR″)₂

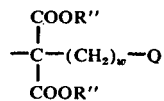

R is hydrogen or lower alkyl
R′ is lower alkyl
R″ is alkyl group having from 6 – 24 carbon atoms
w is an integer from 0 to 4.

Illustrative examples of the compounds shown above are
di-n-octadecyl α-(3,5-di-t-butyl-4-hydroxybenzyl)-malonate
di-n-octadecyl α-(3-t-butyl-4-hydroxy-5-methyl-benzyl)malonate which is disclosed in the Netherlands Patent No. 6,711,199, February 19, 1968
di-n-octadecyl-α,α′bis-(3-t-butyl-4-hydroxy-5-methylbenzyl)malonate which is disclosed in the Netherlands Patent No. 6,803,498, Sept. 18, 1968.

2. Phenolic compounds having the general formula
   Q—R

Illustrative examples of the compounds shown above are
2,6-di-t-butyl-p-cresol
2-methyl-4,6-di-t-butylphenol and the like.

3. Phenolic compounds having the formula
   Q—C_wH_{2w}—Q
2,2′-methylene-bis(6-t-butyl-4-methylphenol)
2,2′-methylene-bis(6-t-butyl-4-ethylphenol)
4,4′-butylidene-bis(2,6-di-t-butylphenol)
4,4′-(2-butylidene)-bis(2-t-butyl-5-methylphenol)
2,2′-methylene-bis[6-(1-methylcyclohexyl)-4-methylphenol and the like.

4. Phenolic compounds having the formula
   R—O—Q
Illustrative examples of such compounds are
2,5-di-t-butylhydroquinone   2,6-di-t-butylhydroquinone 2,5-di-t-butyl-4-hydroxyanisole 5. Phenolic compounds having the formula
   Q—S—Q
Illustrative examples of such compounds are
4,4′-thiobis-(2-t-butyl-5-methylphenol)
4,4′thiobis-(2-t-butyl-6-methylphenol)
2,2′-thiobis-(6-t-butyl-4-methylphenol)

6. Phenolic compounds having the formula

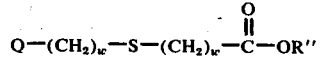

Illustrative examples of such compounds are
octadecyl-(3,5-dimethyl-4-hydroxybenzylthio)-acetate
dodecyl-(3,5-di-t-butyl-4-hydroxybenzylthio)-propionate 7. Phenolic compounds having the formula

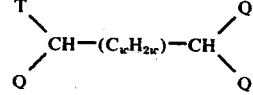

wherein
T is hydrogen
R or Q as defined above.

Illustrative examples of such compounds are
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3′-t-butyl-4′-hydroxy-6′-methylphenyl)-n-pentane 8. Phenolic compounds having the formula

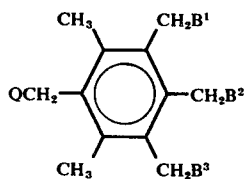

wherein B¹, B² and B³ are hydrogen, methyl or Q, provided that when B¹ and B³ are Q then B² is hydrogen or methyl and when B² is Q then B¹ and B³ are hydrogen or methyl.

Illustrative examples of such compounds are
1,4-di(3,5-di-t-butyl-4-hydroxybenzyl-2,3,5,6-tetramethylbenzene 1,3,5-tri(3,5-di-t-butyl-4-hydroxybenzyl)-2,4,6-trimethylbenzene 9. Phenolic compounds having the formula

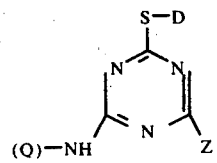

wherein

Z is NHQ, —S—D or —O—Q

D is alkyl group having from 6 — 12 carbon atoms or —(C$_v$H$_{2w}$)-S-R''

Illustrative examples of such compounds are 2,4-bis-(n-octylthio)-6-(3,5-di-t-butyl-4-hydroxyaniline)-1,3,5-triazine 6-(4-hydroxy-3-methyl-5-t-butylanilino)-2,4-bis-(n-octylthio)-1,3,5-triazine 6-(4-hydroxy-3,5-dimethylanilino)-2,4-bis-(n-octylthio)-1,3,5-triazine 6-(4-hydroxy-3,5-di-t-butylanilino)-2,4-bis-(n-octylthioethylthio)-1,3,5-triazine 6-(4-hydroxy-3,5-di-t-butylanilino)-4-(4-hydroxy-3,5-di-t-butylphenoxy)-2-(n-octylthio)-1,3,5-triazine 2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

10. Phenolic compounds having the formula

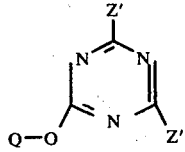

wherein

Z' is —O—Q, —S—D or —S—(C$_w$H$_{2w}$)-SD

Illustrative examples of such compounds are 2,3-bis-(3,5-di-t-butyl-4-hydroxyphenoxy)-6-(n-octylthio)-1,3,5-triazine 2,4,6-tris-(4-hydroxy-3,5-di-t-butylphenoxy)-1,3,5-triazine.

6-(4-hydroxy-3,5-di-t-butylphenoxy)-2,4-bis-(n-octylthioethylthio)-1,3,5-triazine 6-(4-hydroxy-3-methylphenoxy)-2,4-bis-(n-octylthio)-1,3,5-triazine 6-(4-hydroxy-3-t-butylphenoxy)-2,4-bis-(n-octylthioethylthio)-1,3,5-triazine 6-(4-hydroxy-3-methyl-5-t-butylphenoxy)-2,4-bis-(n-octylthio)-1,3,5-triazine 2,4-bis-(4-hydroxy-3-methyl-5-t-butylphenoxy)-6-(n-octylthio)-1,3,5-triazine 2,4,6-tris-(4-hydroxy-3-methyl-5-t-butylphenoxy)-1,3,5-triazine 6-(4-hydroxy-3,5-di-t-butylphenoxy)-2,4-bis-(n-octylthiopropylthio)-1,3,5-triazine 6-(4-hydroxy-3,5-di-t-butylphenoxy)-2,4-bis-(n-dodecylthioethylthio)-1,3,5-triazine 2,4-bis-(4-hydroxy-3,5-di-t-butylphenoxy)-6-butylthio-1,3,5-triazine 2,4-bis-(4-hydroxy-3,5-di-t-butylphenoxy)-6-(n-octadecylthio)-1,3,5-triazine 2,4-bis-(4-hydroxy-3,5-di-t-butylphenoxy)-6-(n-dodecylthio)-1,3,5-triazine 2,4-bis-(4-hydroxy-3,5-di-t-butylphenoxy)-6-(n-octylthiopropylthio)-1,3,5-triazine 2,4-bis-(4-hydroxy-3,5-di-t-butylphenoxy)-6-(n-octylthioethylthio)-1,3,5-triazine 2,4-bis-(4-hydroxy-3,5-di-t-butylphenoxy)-6-(n-dodecylthioethylthio)-1,3,5-triazine The above phenolic triazine stabilizers are more fully described in U.S. Pat. No. 3,255,191.

11. Phenolic compounds having the formula
[Q—C$_z$H$_{2z}$—COO-C$_z$H$_{2z}$]$_p$R'''-(R)$_{4-p}$ wherein p is an integer from 2 to 4 and R''' is a tetravalent radical selected from aliphatic hydrocarbons having from 1 to 30 carbon atoms aliphatic mono and dithioethers having from 1 to 30 carbon atoms aliphatic mono and diethers having from 1 to 30 carbon atoms and z is an integer from 0 to 6.

Illustrative examples of such compounds are

Sub-class I n-Octadecyl 3-(3,5-di-t-butyl-4-hydroxyphenyl)-propionate n-Octadecyl 2-(3,5-di-t-butyl-4-hydroxyphenyl)-acetate n-Octadecyl 3,5-di-t-butyl-4-hydroxybenzoate n-Hexyl 3,5-di-t-butyl-4-hydroxyphenylbenzoate n-Dodecyl 3,5-di-t-butyl-4-hydroxyphenylbenzoate Neo-dodecyl 3-(3,5-di-t-butyl-4-hydroxyphenyl)-propionate Dodecyl β-(3,5-di-t-butyl-4-hydroxyphenyl)-propionate Ethyl α-(4-hydroxy-3,5-di-t-butylphenyl)-isobutyrate Octadecyl α-(4-hydroxy-3,5-di-t-butylphenyl)-isobutyrate Octadecyl α-(4-hydroxy-3,5-di-t-butylphenyl)-propionate Sub-class II 2-(n-octylthio)ethyl 3,5-di-t-butyl-4-hydroxybenzoate 2-(n-octylthio)ethyl 3,5-di-t-butyl-4-hydroxyphenylacetate 2-(n-octadecylthio)ethyl 3,5-di-t-butyl-4-hydroxyphenylacetate 2-(n-octadecylthio)ethyl 3,5-di-t-butyl-4-hydroxy benzoate 2-(2-hydroxyethylthio)ethyl 3,5-di-t-butyl-4-hydroxybenzoate 2,2'-Thiodiethanol bis(3,5-di-t-butyl-4-hydroxyphenyl)acetate Diethyl glycol bis-[3,5-di-t-butyl-4-hydroxyphenyl)-propionate]

2-(n-octadecylthio)ethyl 3-(3,5-di-t-butyl-4-hydroxyphenyl)propionate 2,2'-Thiodiethanol-bis-3-(3,5-di-t-butyl-4-hydroxyphenyl)propionate Stearamido M,N-bis-[ethylene 3-(3,5-di-t-butyl-4-hydroxyphenyl)propionate]

n-Butylimino N,N-bis-[ethylene 3-(3,5-di-t-butyl-4-hydroxyphenyl)propionate]

2-(2-stearoyloxyethylthio)ethyl 3,5-di-t-butyl-4-hydroxybenzoate 2-(2-hydroxyethylthio)ethyl 7-(3-methyl-5-t-butyl-4-hydroxyphenyl)heptanoate 2-(2-stearoyloxyethylthio)ethyl 7-(3-methyl-5-t-butyl-4-hydroxyphenyl)heptanoate

Sub-class III 1,2-propylene glycol bis-[3-(3,5-di-t-butyl-4-hydroxyphenyl)propionate]

Ethylene glycol bis-[3-(3,5-di-t-butyl-4-hydroxyphenyl)propionate]

Neopentylglycol bis-[3-(3,5-di-t-butyl-4-hydroxyphenyl)propionate]

Ethylene glycol bis-(3,5-di-t-butyl-4-hydroxyphenylacetate)

Glycerine-1-n-octadecanoate-2,3-bis-(3,5-di-t-butyl-4-hydroxyphenylacetate

Pentaethylthritol-tetrakis-[3-(3',5'-di-ti-butyl-4'-hydroxyphenyl)propionate]

1,1,1-trimethylol ethane-tris-3-(3,5-di-t-butyl-4-hydroxyphenyl)propionate

Sorbitol hexa-[3-(3,5-di-t-butyl-4-hydroxyphenyl)-propionate]

1,2,3-butanetriol tris-[3-(3,5-di-t-butyl-4-hydroxyphenyl)propionate]

2-hydroxyethyl 7-(3-methyl-5-t-butyl-4-hydroxyphenyl)heptanoate 2-stearoyloxyethyl 7-(3-methyl-5-t-butyl-4-hydroxyphenyl)heptanoate 1,6-n-hexanediol-bis[(3',5'-di-t-butyl-4-hydroxyphenyl)propionate]

The above phenolic ester stabilizers of sub-classes I, II and III are more fully described in U.S. Pat. No. 3,330,859, and U.S. Pat. No. 3,644,482, respectively.

12. Phenolic compounds having the formula

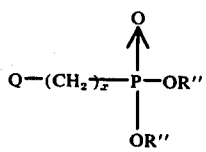

where $x$ is an integer of 1 ro 2.

Illustrative examples of such compounds are

Di-n-octadecyl 3,5-di-t-butyl-4-hydroxybenzyl-phosphonate

Di-n-octadecyl 3-t-butyl-4-hydroxy-5-methyl-benzyl-phosphonate

Di-n-octadecyl 1-(3,5-di-t-butyl-4-hydroxyphenyl)-ethanephosphonate

Di-n-tetradecyl 3,5-di-t-butyl-4-hydroxybenzyl-phosphonate

Di-n-hexadecyl 3,5-di-t-butyl-4-hydroxybenzyl-phosphonate

Di-n-docosyl-3,5-di-t-butyl-4-hydroxybenzyl-phosphonate

Di-n-octadecyl-3,5-di-t-butyl-4-hydroxybenzyl-phosphonate

The above di-(higher)alkyl phenolic phosphonates are more fully described in U.S. Pat. No. 3,281,505.

13. Phenolic compounds having the formula

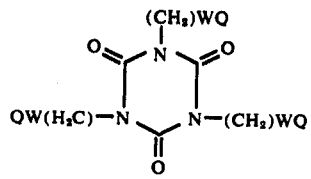

wherein

W and Q are as defined above.

Illustrative examples of such compounds are tris-(3,5-di-t-butyl-4-hydroxybenzyl)isocyanurate tris-(3-t-butyl-4-hydroxy-5-methylbenzyl)isocyanurate The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

The compounds of formula I wherein $R^3$ is an alkyl group, a phenyl group, an alkylene group or a phenylene group may be prepared by reacting a substituted piperazine of the formula

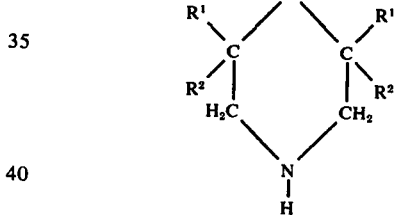

wherein $R^1$ and $R^2$ are as defined above with a mono or di-acid chloride or (lower)alkyl mono or diester of the formula

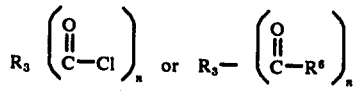

wherein $R_3$ and $n$ are as defined above and $R^6$ is a lower alkyl group of from 1 to 4 carbon atoms. The acylation reaction is carried out by the standard methods known to those skilled in the art.

Illustrative of the mono and dibasic acids which may be converted to the acid halides such as the acid chloride and/or esters include acetic acid, propionic acid, and butyric acid, isobutyric acid, valeric acid, caproic acid, caprylic acid, decanoic acid, dodecanoic acid, pentadecanoic acid, steric acid, behenic acid, tetracosanoic acid, benzoic acid and the like; oxalic acid, malonic acid, succinic acid, 2,3-dimethylsuccinic acid, glutaric acid, 3-methylglutaric acid, adipic acid, suberic acid, azalaic acid, sebacic acid, phthalic acid, isophthalic acid, terephthalic acid and the like. The preferred organic monobasic acids from which the acid halide or ester is derived contains from 1 to 24 carbon atoms and the most preferred contains from 6 to 18 carbon atoms. The preferred organic dibasic acids from which the diacid halide or dialkyl ester is derived contains from 1 to 12 carbon atoms and more preferred contains from 1 to 8 carbon atoms.

The compounds of formula I wherein $R^3$ is a group having the formula

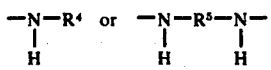     IV wherein $R^4$ and $R^5$ are as defined above may be prepared by reacting a compound of formula II with a mono or diisocyanate having the formula

     V wherein $R^4$ and $R^5$ is as defined above, an inert solvent such as hexane.

Illustrative examples of the monoisocyanates are methylisocyanate, ethylisocyanate, butylisocyanate, isobutylisocyanate, pentylisocyanate, isopentylisocyanate, hexylisocyanate, octylisocyanate, dodecylisocyanate, tetradecylisocyanate, hexadecylisocyanate, octadecylisocyanate, eicosylisocyanate, tetracosylisocyanate, phenylisocyanate, and the like; illustrative examples of diisocyanates are methylenediisocyanate, ethylenediisocyanate, propylenediisocyanate, isopropylenediisocyanate, butylenediisocyanate, pentylenediisocyanate, isopentylenediisocyanate, hexamethylenediisocyanate, octamethylenediisocyanate, decamethylenediisocyanate, p-phenylenediisocyanate, m-phenylenediisocyanate, 2,4-toluenediisocyanate, and the like. The preferred organic mono isocyanates contain from 1 to 24 carbon atoms and the most preferred contains from 6 to 18 carbon atoms. The preferred organic diisocyanates contain from 1 to 12 carbon atoms and the most preferred contains from 1 to 8 carbon atoms.

The compounds of formula II are prepared by reducing a compound of the formula

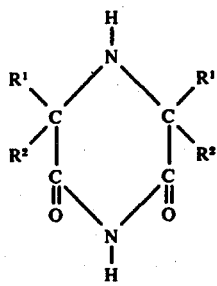     VI with lithium aluminum hydride.

Compounds of formula VI, wherein $R^1$ and $R^2$ form a mono cyclic ring with the carbon to which they are attached, may be prepared by the self condensation of a cycloalkyl amino cyanohydrin according to the procedure described by R. Sudo and S. Ichihera, Bull. Chem. Soc. Japan 36 34 (1963) and subsequent hydrolysis as described by E. F. J. Duynstee et al, Recueil de Chemie des Pays - Bas 87 945 (1968). The cycloalkylamino cyanohydrin is formed by the sequential addition of hydrogen cyanide and ammonia to a cycloalkanone as described by W. E. Noland, R. J. Sundberg and M. L. Michaelson, J. Org. Chem. 28 3576 (1963). Although the above references deal specifically with the cycloalkyl case, the procedures therein have been found to be operable in the alkyl case as well, for example substitution of an alkanone such as acetone for the cycloalkanone such as cyclohexanone in the above procedure.

The preparation of the substituted piperazine diones of formula VI are more fully disclosed in copending application filed on Mar. 24, 1972 (Docket Number GC 586).

The following examples, presented for illustration and not limitation, will further serve to typify the nature of the present invention.

EXAMPLE 1

7,15-diazadispiro[5,1,5,3]hexadecane

In a dry 2-liter Morton flask equipped with stirrer, condenser, dropping funnel and $N_2$ inlet was placed a suspension of 6.43 g. of lithium aluminum hydride in 380 ml. of dry ether. To the suspension was added with stirring under an $N_2$ atmosphere a slurry of 17.6 g. (0.070 moles) of 7, 15-diazadispiro[5,1,5,3]hexadecane-14,16-dione in 700 ml. of ether at such a rate as to maintain gentle reflux. The reaction mixture was allowed to stir for 0.5 hours then heated to boiling under reflux for 21 hours. At the end of this time, the reaction mixture was cooled to 5° C. and water was added carefully dropwise until the precipitated solids became white and granular. The solid precipitate was made filterable by the addition of 400 g. of anhydrous sodium sulfate. The reaction mixture was then filtered with suction and the collected solids were washed well with additional ether. The filtrate and ether washes were combined, dried over anhydrous sodium sulfate and evaporated under reduced pressure. The residue was taken up in a minimum amount of hot benzene and n-hexane was added at the boil until a precipitate formed. The solution was allowed to stand at room temperature about 48 hours followed by filtration to separate a minor amount of solids which formed. The filtrate was cooled to 5° C. for about 14 hours and crystals formed were collected by suction yielding the product as white crystals, m.p. 89°–90° C.

By following the above procedure, and substituting for 7,15-diazadispiro[5,1,5,3]hexadecane-14,16-dione an equivalent amount of:

a. 2,2,6,6-tetramethyl-3,5-diketopiperazine
b. 1,9-dimethyl-7,15-diazadispiro[5,1,5,3]hexadecane-14,16-dione there is respectively obtained the following compounds:

a. 2,2,6,6-tetramethylpiperazine
b. 1,9-dimethyl-7,15-diazadispiro[5,1,5,3]hexadecane.

EXAMPLE 2

15-stearoyl- 7,15-diazadispiro[5,1,5,3]hexadecane

In a 500 ml. 3-necked flask equipped with stirrer, condenser with drying tube, thermometer, dropping funnel and nitrogen inlet was placed a solution of 15.6 g. (0.07 moles) of 7,15-diazadispiro[5,1,5,3]hexadecane in 150 ml. of dry pyridine. Under a dry nitrogen atmosphere, the solution was cooled to 5° C with an external ice bath and a solution of 21.2 g. (0.07 moles) of stearoyl chloride in 50 ml. of hexane was added dropwise with stirring over a 20 minute period. The reaction mixture was then allowed to warm to room temperature and stir for about 16 hours. The reaction mixture was filtered and the filtrate was taken up in ether, washed well with water, then with 2N NaOH solution. The filtrate was again filtered by suction, and the ether solution dried over anhydrous sodium sulfate and concentrated to dryness under reduced pressure. The residue was recrystallized from acetonitrile, yielding colorless crystals, m.p. 56°–59° C.

By following the above procedure, and substituting for the stearoyl chloride an equivalent amount of:
 a. oxalyl dichloride
 b. benzoyl chloride
 c. phthaloyl chloride
 d. isophthaloyl chloride
 e. terephthaloyl chloride
 f. docosanoyl chloride there is respectively obtained the following compounds:
  a. 15,15'-oxalyl-bis-(7'',15'''-diazadispiro[5,1,5,3]hexadecane)
  b. 15-benzoyl-7,15-diazadispiro[5,1,5,3]hexadecane; m.p. 97°–99° C
  c. 15,15'-phthaloyl-bis-(7'',15''-diazadispiro[5,1,5,3]hexadecane)
  d. 15,15'-isophthaloyl-bis-(7'',15''-diazadispiro[5,1,5,3]hexadecane)
  e. 15,15'-terephthaloyl-bis-(7'',15''-diazadispiro[5,1,5,3]hexadecane)
  f. 15-docosanoyl-7,15-diazadispiro[5,1,5,3]hexadecane; m.p. 67°–69°

EXAMPLE 3

By essentially following the procedure of Example 2 and substituting for 7,15-diazadispiro [5,1,5,3]hexadecane and stearoyl chloride, an equivalent amount of the following reactants:
 a. 2,2,6,6-tetramethylpiperazine + stearoyl chloride
 b. 2,2,6,6-tetramethylpiperazine + oxalyl dichloride
 c. 2,2,6,6-tetramethylpiperazine + terephthaloyl dichloride
 d. 2,2,6,6-tetramethylpiperazine + benzoyl chloride
 e. 1,9-dimethyl-7,15-diazadispiro[5,1,5,3]hexadecane + stearoyl chloride there is respectively obtained the following compounds:
  a. 4-stearoyl-2,2,6,6-tetramethylpiperazine, m.p. 33°–35° C
  b. 4,4'-oxalyl-bis[2,2,6,6-tetramethylpiperazine)
  c. 4,4'-terephthaloyl-bis(2,2,6,6-tetramethylpiperazine
  d. 4-benzoyl-2,2,6,6-tetramethylpiperazine
  e. 15-stearoyl-1,9-dimethyl-7,15-diazadispiro[5,1,5,3]hexadecane.

EXAMPLE 4

15-acetyl-7,15-diazadispiro [5,1,5,3]hexadecane

In a 200 ml 3-necked flask equipped with a stirrer, thermometer and condenser with drying tube was placed a solution of 4.00 g. (0.018 moles) of 7,15-diazadispiro[5,1,5,3]hexadecane in 50 ml of glacial acetic acid. To this solution, 1.76 g. (0.018 moles) of acetic anhydride was added in one portion and the reaction mixture was allowed to stir at room temperature overnight. At the end of this time, the reaction mixture was poured onto ice, the aqueous solution was made slightly alkaline by the addition of 50% sodium hydroxide, and the solution was extracted with ether. The ether extracts were combined, dried over anhydrous sodium sulfate and concentrated under reduced pressure. The crude product was purified by recrystallization from heptane, giving colorless crystals, m.p. 104°–107° C.

In a similar manner, by substituting for 7,15-diazadispiro[5,1,5,3]hexadecane an equivalent amount of:
 a. 2,2,6,6-tetramethylpiperazine
 b. 1,9-dimethyl-7,15-diazadispiro[5,1,5,3]hexadecane there is respectively obtained the following compounds:
  a. 4-acetyl-2,2,6,6-tetramethylpiperazine
  b. 15-acetyl-1,9-dimethyl-7,15-diazadispiro[5,1,5,3]hexadecane.

EXAMPLE 5

15,15'-sebacoyl-bis(7'',15''-diazadispiro[5,1,5,3]hexadecane)

4.5 g. (0.02 moles) of 7,15-diazadispiro[5,1,5,3]hexadecane, 2.3 g. (0.01 moles) of dimethyl sebacate and 10 ml. of benzene was placed in a 25 ml. 2-necked flask equipped with a thermometer, claisen distillation head, nitrogen capillary inlet and distillation received. The benzene was slowly distilled from the reaction mixture, and the residue was heated to 200° C. by an oil bath. The reaction mixture was held at this temperature for 3 hours, and about 0.4 ml. of methanol distillate was recovered in the receiver. The oil bath temperature was slowly raised to 235° C for 1 hour and then the reaction mixture was placed under a vacuum of 15 mm. for 0.75 hours. The reaction mixture was allowed to cool to room temperature, the vacuum released and the residue was triturated with warm hexane. After trituration, the partially crystalline material obtained was recrystallized twice from acetone, yielding colorless crystals, m.p. 105°–109° C.

By following the above procedure and substituting for dimethyl sebacate an equivalent amount of:
 a. dimethyl succinate
 b. dimethyl malonate
 c. dimethyl suberate
 d. dimethyl glutarate
 e. dimethyl adipate
 f. dimethyl pimelate
 g. dimethyl azelate there is respectively obtained the following compounds:
  a. 15,15'-succinoyl-bis(7'',15''-diazadispiro[5,1,5,3]hexadecane)
  b. 15,15'-malonyl-bis(7'',15''-diazadispiro[5,1,5,3]hexadecane); m.p. 158–162°
  c. 15,15'-suberoyl-bis(7'',15''-diazadispiro[5,1,5,3]hexadecane)
  d. 15,15'-glutaroyl-bis(7'',15''-diazadispiro[5,1,5,3]hexadecane)
  e. 15,15'-adipoyl-bis(7'',15''-diazadispiro[5,1,5,3]hexadecane); m.p. 160°–162°
  f. 15,15'-pimeloyl-bis(7'',15''-diazadispiro[5,1,5,3]hexadecane)
  g. 15,15'-azeloyl-bis(7'',15''-diazadispiro[5,1,5,3]hexadecane)

Similarly, 4,4'-sebacoyl-bis(2,2,6,6-tetramethylpiperazine is prepared by substituting for 7,15-diazadispiro[5,1,5,3]hexadecane an equivalent amount of 2,2,6,6-tetramethylpiperazine.

EXAMPLE 6

15-(n-octadecylcarbamoyl)-7,15-diazadispiro[5,1,5,3]hexadecane

In a 200 ml. 1-necked flask was placed a solution of 1.9 g. (0.0085 moles) of 7,15-diazadispiro[5,1,5,3]hexadecane, and 2.5 g. (0.0085 moles) of stearyl isocyanate in 50 ml. of hexane. The reaction mixture was swirled to dissolve the solids and then allowed to stand for 2 hours at room temperature. A precipitate formed and the reaction mixture was warmed to redissolve the precipitate, then cooled. The resulting precipitate was collected, washed with cold hexane, and recrystallized from hexane, yielding colorless crystals, m.p. 77°–78° C.

By following the above procedure and substituting for 7,15-diazadispiro[5,1,5,3]hexadecane an equivalent amount of each of the following:

a. 2,2,6,6-tetramethyl-3,5-diketopiperazine
b. 1,9-dimethyl-7,15-diazadispiro[5,1,5,3]hexadecane there is respectively obtained the following compounds:

a. 4-(n-octadecylcarbamoyl)-2,2,6,6-tetramethylpiperazine
b. 15-(n-octadecylcarbamoyl)-1,9-dimethyl-7,15-diazadispiro[5,1,5,3]hexadecane.

EXAMPLE 7

By essentially following the procedure of Example 6 and substituting for the reactants used, namely, 7,15-diazadispiro[5,1,5,3]hexadecane and stearyl isocyanate, an equivalent amount of the following reactants:

a. 2,2,6,6-tetramethylpiperazine + toluene diisocyanate
b. 2,2,6,6-tetramethylpiperazine + phenyl isocyanate
c. 7,15-diazadispiro[5,1,5,3]hexadecane + p-phenylene diisocyanate
d. 7,15-diazadispiro[5,1,5,3]hexadecane + methyl isocyanate
e. 7,15-diazadispiro[5,1,5,3]hexadecane + hexamethylene diisocyanate there is respectively obtained the following compounds:

a. 4-(2''-methyl-1'',5''-phenylenedicarbamoyl)-2,2,6,6-tetramethylpiperazine
b. 4-(phenylcarbamoyl)2,2,6,6-tetramethyl-piperazine
c. 15,15'-(p-phenylenedicarbamoyl)-bis-7,15-diazadispiro[5,1,5,3]hexadecane
d. 15-(methylcarbamoyl)-7,15-diazadispiro[5,1,5,3]hexadecane
e. 15,15'-(hexamethylenedicarbamoyl)-bis-(7,15-diazadispiro[5,1,5,3]hexadecane)

EXAMPLE 8

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The test conducted on polymers using an artificial light exposure device is described below:

a. Sample Preparation

5 Mil Film - Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sunlamps and black lights (20 of each). The 5 mil sample film are mounted on 3 × 2'' IR card holders with ¼inch × 1 inch windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

Table I

| Formulation* | Time in Hours to .5 Carbonyl Absorbance Units |
|---|---|
| 0.5% 15-stearoyl-7,15-diazadispiro[5,1,5,3]hexadecane | 1450 |
| 0.5% 15-benzoyl-7,15-diazadispiro[5,1,5,3]hexadecane | 670 |
| 0.5% 15-acetyl-7,15-diazadispiro[5,1,5,3]hexadecane | 1535 |
| 0.5% 15,15'-sebacoyl-bis(7'',15''-diazadispiro[5,1,5,3]hexadecane) | 1540 |
| 0.5% 15-(n-octadecylcarbamoyl)-7,15-diazadispiro[5,1,5,3]hexadecane | 960 |
| 0.5% 4-stearoyl-2,2,6,6-tetramethylpiperazine | 1635 |
| 0.5% 15,15'-malonyl-bis(7'',15''-diazadispiro[5,1,5,3]hexadecane) | 2540 |
| 0.5% 15-docosanoyl-7,15-diazadispiro[5,1,5,3]hexadecane | 1460 |
| 0.5% 15,15'-adipoyl-bis(7'',15''-diazadispiro[5,1,5,3]hexadecane) | 1800 |
| 0.5% 15,15'-(n-hexamethylenedicarbamoyl-bis-(7'',15''-diazadispiro[5,1,5,3]hexadecane | 1510 |
| Control* | 270 |

*Each of the samples tested and the control contains 0.2% of (di-n-octadecyl(3,5-di-t-butyl-4-hydroxybenzyl) phosphonate which is an antioxidant which prevents oxidative degradation of polypropylene.

Other hindered phenolic antioxidants may be used in place of di-octadecyl(3,5-di-t-butyl-4-hydroxybenzyl)phosphonate in the above mentioned compositions for example, di-n-octadecyl α-(3-t-butyl-4-hydroxy-5-methylbenzyl)malonate, 2,4-bis-(n-octylthio)-6-(3,5-di-t-butyl-4-hydroxyanilino)-1,3,5-triazine, octadecyl 3-(3',5'-di-t-butyl-4'-hydroxyphenyl)propionate, pentaethylthritol-tetrakis[3-(3,5-di-t-butyl-4-hydroxyphenyl)propionate], tris-(3,5-di-t-butyl-4-hydroxybenzyl)isocyanurate respectively.

EXAMPLE 9 a. A composition comprising acrylonitrile-butadiene-styrene terpolymer and 1% by weight of 4,4'-oxalyl-bis(2,2,6,6-tetramethylpiperazine) resists embrittlement due to exposure to ultraviolet light longer than one which does not contain the stabilizer.

b. A composition comprising a polyurethane prepared from toluene diisocyanate and alkylene polyols and 1.0% by weight of 4-acetyl-2,2,6,6-tetramethylpiperazine is more stable to sunlight, fluorescent sunlamps, black lights and fluorescent lights than the unformulated polyurethane.

c. A composition comprising a polycarbonate prepared from bisphenol-A and phosgene and 1% by weight of 4-(2-methyl-1,5-phenylenedicarbamoyl)-2,2,6,6-tetramethylpiperazine resists discoloration due to exposure to ultraviolet light longer than one which does not contain the stabilizer.

d. A composition comprising a polyester (polyethyleneterephthalate) and 0.2% by weight of 15,15'-(p-phenylenedicarbamoyl)-7,15-diazadispiro[5,1,5,3]hexadecane resists discoloration due to exposure to ultraviolet light longer than one which does not contain the stabilizer.

e. A composition comprising polymethylmethacrylate and 0.25% by weight of 15,15'-(hexamethylenedicarbamoyl)-bis(7,15-diazadispiro[5,1,5,3-]hexadecane) resists discoloration due to exposure to ultraviolet light longer than one which does not contain the stabilizer.

EXAMPLE 10 a. A stabilized linear polyethylene is prepared by incorporating therein 0.5% by weight of 15,15'-oxalyl-bis-(7,15-diazadispiro[5,1,5,3]hexadecane). The stabilized compositions resist embrittlement due to exposure to ultraviolet light longer than one which does not contain the stabilizer.

b. A stabilized polyamide (nylon 6,6) is prepared by incorporating therein 0.1% of 15,15'-phthaloyl-bis-(7,15-diazadispiro[5,1,5,3]hexadecane. The light stability of the stabilized composition is superior to that of an unstabilized polyamide.

c. A stabilized polyphenylene oxide polymer (prepared by polymerizing 2,6-dimethylphenol) is prepared by incorporating therein 0.5% by weight 4-stearoyl-2,2,6,6-tetramethylpiperazine. The stabilized compositions resist embrittlement due to exposure to ultraviolet light longer than one which does not contain the stabilizer.

d. A stabilized crystalline polystyrene is prepared by incorporating therein 0.1% by weight of 4,4'-terephthaloyl-bis(2,2,6,6-tetramethylpiperazine). The stabilized compositions resist embrittlement due to exposure to ultraviolet light longer than one which does not contain the stabilizer.

EXAMPLE 11

High impact polystyrene resin containing elastomer (i.e., butadiene-styrene) is stabilized against loss of elongation properties due to exposure to ultraviolet light by incorporation of 0.3% by weight of 15-acetyl-7,15-diazadispiro[5,1,5,3]hexadecane.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into a sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portion of the strips are placed in an FS/BL chamber according to Example 6 (b) except that the time to 50% reduction in elongation is measured. The stabilized polystyrene resin retains its elongation property longer than the unstabilized resin.

Similar results are obtained when an equivalent amount of the following stabilizers are used in place of the above mentioned stabilizer.

a. 0.1% by weight of 15-benzoyl-7,15-diazadispiro[5,1,5,3]hexadecane b. 0.2% by weight of 15,15'-isophthaloyl-bis-(7,15-diazadispiro[5,1,5,3]hexadecane)

c. 1.0% by weight of 15,15'-phthaloyl-bis-(7,15-diazadispiro[5,1,5,3]hexadecane)

d. 0.1% by weight of 15,15'-terephthaloyl-bis-(7,15-diazadispiro[5,1,5,3]hexadecane)

e. 0.5% by weight of 15-acetyl-1,9-dimethyl-7,15-diazadispiro[5,1,5,3]hexadecane f. 0.5% by weight of 15,15'-succinoyl-bis-(7,15-diazadispiro[5,1,5,3]hexadecane)

g. 0.5% by weight of 15,15'-malonyl-bis 7,15-diazadispiro[5,1,5,3]hexadecane)

h. 0.5% by weight of 15,15'-suberoyl-bis-(7,15-diazadispiro[5,1,5,3]hexadecane i. 0.5% by weight of 4-(n-octadecylcarbamoyl)-2,2,6,6-tetramethylpiperazine j. 0.5% by weight of 15-methylcarbamoyl)-7,15-diazadispiro[5,1,5,3]hexadecane.

Antioxidants may also be incorporated into each of the above mentioned compositions for example, di-n-octadecyl-α,α'-bis(3-t-butyl-4-hydroxy-5-methylbenzyl) malonate, 2,4-bis(4-hydroxy-3,5-di-t-butylphenoxy)-6-(n-octylthioethylthio)-1,3,5-triazine, 2,4-bis(3,5-di-t-butyl-4-hydroxyphenoxy)-6-(n-octylthio)-1,3,5-triazine di-n-octadecyl 3,5-di-t-butyl-4-hydroxybenzyl phosphonates and octadecyl 3(3',5'-di-t-butyl-4-hydroxyphenyl)propionate respectively.

What is claimed is:

1. A compound of the formula

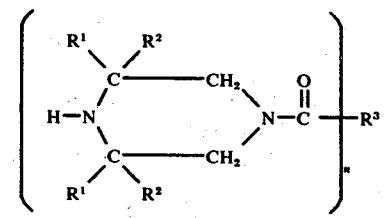

wherein
R¹ and R² together with the carbon to which they are bound form a cyclopentyl or cyclohexyl ring, which is unsubstituted or substituted with a methyl group;
n is an integer from 1 to 2;
when n is 1, R³ is alkyl having from 1 to 24 carbon atoms, a phenyl group, or a group having the formula

wherein R⁴ is alkyl having from 1 to 24 carbon atoms or phenyl;
when n is 2, R³ is alkylene having from 1 to 10 carbon atoms, a carbon to carbon bond, a phenylene group or the group having the formula

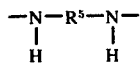

wherein R⁵ is alkylene having from 1 to 10 carbon atoms, a phenylene or (lower)alkyl substituted phenylene group.

2. A compound according to claim 1 having the formula

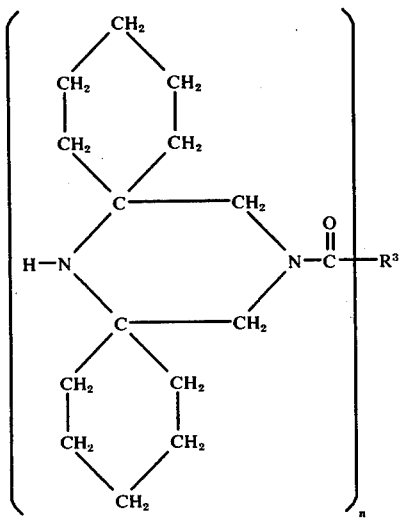

wherein n is 1 or 2;
when n is 1, R³ is alkyl having from 1 to 24 carbon atoms, a phenyl group, or a group having the formula

wherein R⁴ is alkyl having from 1 to 24 carbon atoms or phenyl;
when n is 2, R³ is alkylene having from 1 to 10 carbon atoms, a carbon to carbon bond, a phenylene group or the group having the formula

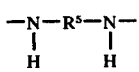

wherein R⁵ is alkylene having from 1 to 10 carbon atoms, a phenylene or (lower)alkyl substituted phenylene group.

3. A compound according to claim 2 wherein n is 1 or 2;
when n is 1, R³ is alkyl having from 6 to 18 carbon atoms, a phenyl group or group having the formula
where R⁴ is alkyl having from 6 to 18 carbon atoms or phenyl;
when n is 2, R³ is alkylene having from 1 to 6 carbon atoms, a phenylene group or the group having the formula

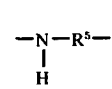

wherein R⁵ is alkylene having from 1 to 6 carbon atoms, a phenylene or (lower)alkyl substituted phenylene group.

4. A compound according to claim 1 which is 15-stearoyl-7,15-diazadispiro[5,1,5,3]hexadecane.

5. A compound according to claim 1 which is 15-stearoyl-1,9-dimethyl-7,15-diazadispiro[5,1,5,3]hexadecane.

6. A compound according to claim 1 which is 15-benzoyl-7,15-diazadispiro[5,1,5,3]hexadecane.

7. A compound according to claim 1 which is 15-acetyl-7,15-diazadispiro[5,1,5,3]hexadecane.

8. A compound according to claim 1 which is 15,15'-sebacoyl-bis(7,15-diazadispiro[5,1,5,3]hexadecane).

9. A compound according to claim 1 which is 15-(n-octadecylcarbamoyl)-7,15-diazadispiro[5,1,5,3]hexadecane.

10. A compound according to claim 1 which is 15-(methylcarbamoyl)-7,15-diazadispiro[5,1,5,3]hexadecane.

11. A compound according to claim 1 which is 15,15'-malonyl-bis(7'',15''-diazadispiro[5,1,5,3]hexadecane.

12. A compound according to claim 1 which is 15-docosanoyl-7,15-diazadispiro[5,1,5,3]hexadecane.

13. A compound according to claim 1 which is 15,15'-adipoyl-bis(7'',15''-diazadispiro[5,1,5,3]hexadecane.

14. A compound according to claim 1 which is 15,15'-(n-hexamethylenedicarbamoyl)-bis(7'',15''-diazadispiro[5,1,5,3]hexadecane.

15. A composition of matter stabilized against ultraviolet deterioration consisting essentially of a synthetic organic polymer normally subject to ultraviolet deterioration containing from 0.01% to 2% by weight of the polymer of a stabilizing compound according to claim 1.

16. A composition of matter stabilized against ultraviolet deterioration consisting essentially of a synthetic organic polymer normally subject to ultraviolet deterioration containing a stabilizing amount of a hindered phenolic antioxidant and from about 0.01% to 2% by weight of the polymer of a compound according to claim 1.

17. A composition of claim 16 wherein the polymer is a polyolefin.

18. A composition of claim 17 wherein the polyolefin is polypropylene.

19. A composition of claim 17 wherein the hindered phenolic compound is selected from n-octadecyl 3-(3,5-di-t-butyl-4-hydroxyphenyl)propionate, di-n-octadecyl(3,5-di-t-butyl-4-hydroxybenzyl)phosphonate, pentaerythritol-tetrakis[3-(3,5-di-t-butyl-4-hydroxyphenyl)propionate], and tris-(3,5-di-t-butyl-4-hydroxybenzyl)isocyanurate.

20. A composition of claim 17 wherein the antixodiant is di-n-octadecyl(3,5-di-t-butyl-4-hydroxybenzyl)-phosphonate.

21. A composition of claim 17 wherein the substituted piperazine stabilizing compound is 15,15'-sebacoyl-bis(7'',15''-diazadispiro[5.1.5.3]hexadecane).

22. A composition of claim 17 wherein the substituted piperazine stabilizing compound is 15,15'-malonylbis(7'',15''-diazadispiro[5.1.5.3]hexadecane).

23. A composition of claim 17 wherein the substituted piperazine stabilizing compound is 15,15'-adipoyl-bis(7'',15''-diazadispiro[5.1.5.3]hexadecane).

* * * * *